US006395006B1

(12) United States Patent
Burchett (10) Patent No.: US 6,395,006 B1
(45) Date of Patent: May 28, 2002

(54) CONNECTOR ASSEMBLY FOR MATING COMPONENTS, CONNECTOR ASSEMBLY FOR A BONE CEMENT MIXING AND DELIVERY SYSTEM, AND BONE CEMENT CONTAINER HAVING A CONNECTOR ASSEMBLY

(75) Inventor: Ronnie Burchett, Missoula, MT (US)

(73) Assignee: Telios Orthopedic Systems, Inc, Missoula, MT (US)

( * ) Notice: Subject to any disclaimer, the term of this patent is extended or adjusted under 35 U.S.C. 154(b) by 0 days.

(21) Appl. No.: 09/503,877

(22) Filed: Feb. 14, 2000

(51) Int. Cl.[7] .............................................. A61B 17/56
(52) U.S. Cl. ......................................... 606/93; 606/92
(58) Field of Search .............................. 606/93, 92, 94, 606/95; 206/219; 222/391, 327, 326; 285/360, 361, 376, 396, 401, 402

(56) References Cited

U.S. PATENT DOCUMENTS

| 4,466,435 A | | 8/1984 | Murray ................... 128/303 R |
| 4,966,601 A | * | 10/1990 | Draenert ....................... 606/92 |
| 5,145,276 A | * | 9/1992 | Demange .................... 403/349 |
| 5,265,956 A | | 11/1993 | Nelson et al. ............... 366/139 |
| 5,344,232 A | | 9/1994 | Nelson et al. ............... 366/139 |
| 5,415,474 A | | 5/1995 | Nelson et al. ............... 366/139 |
| 5,431,654 A | | 7/1995 | Nic .............................. 606/92 |
| 5,456,670 A | * | 10/1995 | Neer et al. ................... 604/155 |
| 5,545,460 A | | 8/1996 | Tanaka et al. ............... 428/137 |
| 5,558,136 A | | 9/1996 | Orrico ......................... 141/23 |
| 5,588,745 A | | 12/1996 | Tanaka et al. ............... 366/130 |
| 5,797,679 A | | 8/1998 | Grulke et al. ............... 366/139 |
| 5,842,785 A | | 12/1998 | Brown et al. ............... 366/139 |

* cited by examiner

Primary Examiner—Nicholas D. Lucchesi
Assistant Examiner—Melba Bumgarner
(74) Attorney, Agent, or Firm—Dorsey & Whitney LLP

(57) ABSTRACT

A connector assembly for a fluid containment system includes a first body and a second body. The first body includes a male end portion having a plurality of fingers extending outwardly and arcuately along the body, a terminating portion of each finger elastically urgable in an inward direction. The second body includes a female end portion having a plurality of longitudinally extending receiving slots along an inner surface of the female portion, each longitudinal slot positioned to axially receive in assembly a respective one of the fingers, and a recess formed in the female portion inner surface adjacent and arcuately offset from each longitudinal slot. The first body is axially loaded into the second body by inserting the fingers into the slots, and the loaded first body is rotated relative to the second body, inwardly urging the fingers, and receiving the fingers within the respective slots.

28 Claims, 7 Drawing Sheets

CONNECTOR ASSEMBLY FOR MATING COMPONENTS, CONNECTOR ASSEMBLY FOR A BONE CEMENT MIXING AND DELIVERY SYSTEM, AND BONE CEMENT CONTAINER HAVING A CONNECTOR ASSEMBLY

TECHNICAL FIELD

This invention pertains in general to connector assemblies for mating components. More particularly, this invention relates to connector assemblies for a bone cement mixing and delivery system.

BACKGROUND OF THE INVENTION

Reconstructive bone surgery is a common procedure to replace bone structures. For example, replacement hip surgery uses a prosthetic hip joint to replace a patient's hip joint. Such surgical procedures include removing the hip joint from a femur, packing bone cement within an inner canal of the femur, and positioning the prosthetic hip joint into the bone cement inside the femur. Subsequently, the cement is allowed to harden, thereby securing the hip joint in place. A tip that is secured to a bone cement dispensing apparatus or container is commonly used to issue bone cement into a bone canal of the femur.

Typically, a bone cement delivery apparatus has a plurality of components that are used during the surgical procedure, for example, a bone cement mixing bowl, a nozzle, one or more delivery tips, a cement container and a dispensing gun just to list a few. Typical bone cement is a fast hardening variety which includes a liquid monomer and a powder that are used together to form a polymer. Once the two ingredients are brought together, for example, in a bone cement mixing bowl, optimal lapsed time for having the ingredients thoroughly mixed is from 2 to 5 minutes, and preferably approximating 2 minutes. After 2 minutes, the bone cement begins to harden. Accordingly, the nature of the cement establishes time restraints in which bone replacement surgery depends and must be structured around. Since time in the surgical room, the surgical team itself, and even the bone cement are expensive propositions, any delays (expected or unexpected) must be minimized.

Adding to the time needed to prepare the bone cement is the process of connecting and disconnecting the various components of the bone cement delivery apparatus. For example, once the ingredients of bone cement are combined in a mixing bowl, the bone cement is typically transported to a container, and the container is threaded to a dispensing gun at one end and threaded to a nozzle and/or tip at the other end. Given the time constraints of the hardening cement and inherent time pressures of a surgical procedure, surgical nurses/assistants assembling the delivery apparatus commonly cross thread the components. Such components are rendered useless because bone cement leaks between the cross-threaded components, and therefore, the preparation process must begin anew. Moreover, threaded component designs have a tendency to collect the bone cement in the grooves which can further increase the risk of cross threading.

Therefore, there exists a need for an improved bone cement delivery apparatus wherein components are interchangeable for different steps in the preparation process and the mating cooperation is improved to increase ease, efficiency and speed for mating one component to another.

SUMMARY OF THE INVENTION

A connector assembly is designed that uses a minimal of time and effort to mate components, for example, components of a bone cement mixing and delivery system.

According to one aspect of the invention, a connector assembly for a fluid containment system includes a first body and a second body. The first body includes a male portion having a plurality of fingers extending outwardly and arcuately along the body, a terminating portion of each finger elastically urgable in an inward direction. The second body includes a female portion having a plurality of longitudinally extending receiving slots along an inner surface of the female portion, each longitudinal slot positioned to axially receive in assembly a respective one of the fingers, and a recess formed in the female portion inner surface adjacent and arcuately offset from each longitudinal slot. The first body is axially loaded into the second body by inserting the fingers into the slots, and the loaded first body is rotated relative to the second body, inwardly urging the fingers, and receiving the fingers within the respective slots.

According to another aspect of the invention, a connector assembly for a bone cement mixing and delivery system includes a bone cement container and a bone cement mixing and delivery system body. The bone cement container includes a cylindrical male portion having a plurality of fingers extending radially outwardly and arcuately along the container, a terminating end portion of each finger elastically urgable in an inward direction. The bone cement mixing and delivery system body includes a female portion having a plurality of longitudinally extending receiving slots along an inner surface of the female portion, each longitudinal slot positioned to axially receive in assembly a respective one of the fingers, and a recess formed in the female portion inner surface adjacent and arcuately offset from each longitudinal slot. The container is axially loaded into the body by inserting the fingers into the slots, and the loaded container is rotated relative to the body, inwardly urging the fingers, and receiving the fingers within the respective slots.

BRIEF DESCRIPTION OF THE DRAWINGS

Preferred embodiments of the invention are described below with reference to the following accompanying drawings depicting examples embodying the best mode for practicing the invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Reference will now be made to a preferred embodiment of Applicant's invention. One exemplary implementation is described below and depicted with reference to the drawings. While the invention is described via a preferred embodiment, it is understood that the description is not intended to limit the invention to this embodiment, but is intended to cover alternatives, equivalents, and modifications such as are included within the scope of the appended claims.

Figures 1, 2:
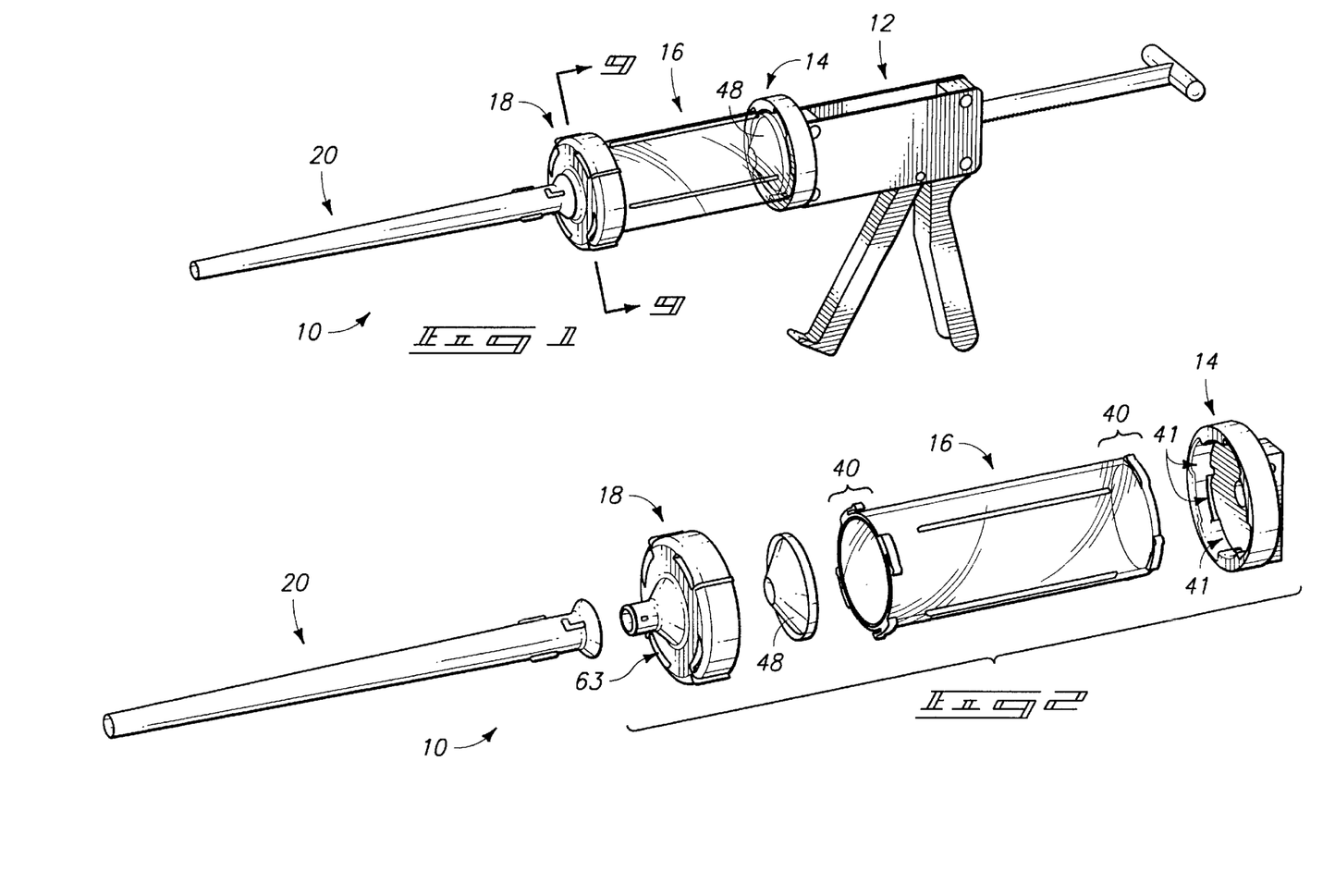
FIG. 1 is a perspective view of a bone cement delivery apparatus, configured in the form of a dispensing gun, the components including an extrusion (or dispensing) gun mechanism, an end cap, a dispensing container, a nozzle and a tubular dispensing tip according to one aspect of the invention.
FIG. 2 is an exploded perspective view of the bone cement dispensing apparatus of FIG. 1 without the extrusion gun mechanism.

FIG. 1 illustrates a perspective view of a bone cement delivery system comprising a dispensing gun, generally indicated by reference numeral 10. Dispensing gun 10 comprises an extrusion gun, or dispensing gun, mechanism 12; an end cap 14; a dispensing container, or cartridge 16; a dispensing nozzle, or nozzle, 18; and a tubular dispensing tip 20. An exemplary material for the dispensing container 16 comprises a clear, relatively rigid, polycarbonate. A clear dispensing container 16 allows for bone cement inspection such as visually judging remaining quantity during a surgical procedure.

An exemplary surgical procedure for using the bone cement delivery system 10, such as replacement hip surgery, begins by placing the tubular dispensing tip 20 inside the hollowed canal of a long bone, such as a femur. Bone cement (not shown) has already been prepared inside dispensing container 16. The extrusion gun 12 applies force to a piston head 48 slidingly cooperating within the dispensing container 16, thereby forcing the bone cement from the dispensing container 16, nozzle 18, and tubular dispensing tip 20 into the bone.

FIG. 2 illustrates the components of the bone cement delivery system, without the extrusion gun mechanism 12, readied for assembly. The dispensing container 16 comprises a cartridge having male portions, or male end portions 40, of a connector assembly provided on opposite ends to enable the same cooperation with other components of the bone cement delivery system, for example, the nozzle 18 and end cap 14. End cap 14 comprises female portions, or female end portions 41, of the connector assembly configured to receive the male portions 40 for mating the components together, and is described below in greater detail. Nozzle 18 also includes such female portions 41.

According to one aspect of the invention, a connector assembly comprises a first connector, male portion, 40, and a second complementary connector, female portion, 41. Male portion 40 and female portion 41 cooperate in assembly to secure a first body to a second body. In one case, container 16 provides the first body, and nozzle 18 provides the second body. Optionally, end cap 14, a funnel 31 (of FIG. 3), or a base 34 (of FIG. 3) form the second body.

According to another aspect, the first body includes a pair of male portions 40; for example, where dispensing container 16 forms the first body, and the second body includes a complementary female portion 41; for example, where nozzle 18 forms the second body. It should be understood that the second body includes one or more female portions 41. Furthermore, the second body can be provided by a variety of components; for example, support base 34 (see FIG. 3), delivery funnel 31 (see FIG. 3), and/or end cap 14 for extrusion gun mechanism 12.

Details of the manner in which nozzle 18 is connected with tubular dispensing tip 20 are disclosed In Applicant's co-pending U.S. patent application Ser. No. 09/503,947, entitled "Delivery Apparatus, Nozzle, and Removable Tip Assembly", and naming inventors as Ronnie Burohett and Randy Scot Wills and filed concurrently herewith. Such U.S. patent application Ser. No. 09/503,947 is herein incorporated by reference as evidencing one manner in which to secure nozzle 18 to tubular dispensing tip 20.

Figure 3:
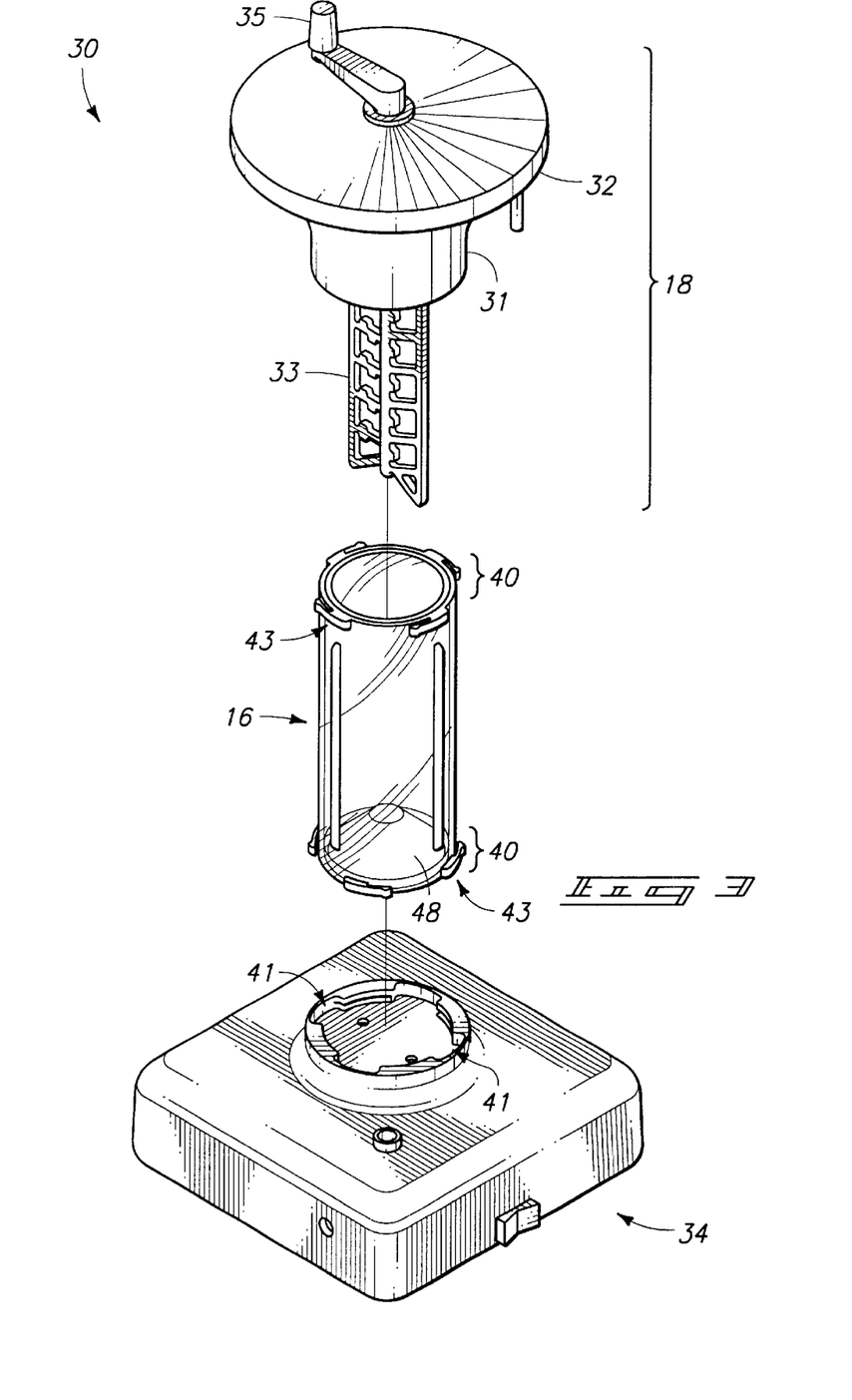
FIG. 3 is an exploded perspective view of a bone cement preparation apparatus using the dispensing container of FIG. 1 as a mixing container according to one aspect of the invention.

FIG. 3 illustrates a bone cement mixing system, generally indicated by reference numeral 30. Dispensing container 16 comprises a mixing and delivery cartridge that is secured to base 34 at one end, and a funnel assembly 36 at an opposite end. Funnel assembly 36 includes a delivery funnel 31, a removable cover 32, mixing blade handle 35, and a mixing blade 33. Handle 35 is rigidly affixed to blade 33, with handle 35 and blade 33 being supported for rotation by cover 32. A bottom end of funnel 31 includes a female connector having longitudinal slots configured similar to receiving recesses 60 (of FIG. 4). Such recesses are configured to axially receive individual fingers 43 of male portion 40. According to one construction, the female connector of funnel 31 here includes a circumferential gasket that seals with male portion 40. Optionally, funnel 31 can be further provided with rotational engaging features present on female portion 41 of base 34 (of FIG. 3). As shown in FIG. 3, mixing blade 33 is rotatably secured to the cover 32 with handle 35 and blade 33 is positioned longitudinally within dispensing container 16. Upon providing ingredients inside the dispensing container 16, the mixing blade 33 is rotated by handle 35 in order to mix the ingredients so as to form, for example, bone cement. Using the dispensing container 16 for mixing ingredients in one procedure and as a container in another procedure illustrates the versatility of the dispensing container 16. Such versatility is further enhanced by the cooperation of male portion 40 and female portion 41 of the connector assembly.

Further details of base 34 are disclosed in Applicant's copending U.S. patent application Ser. No. 09/503,946, entitled "Self-Contained Base for a Surgical Cement Mixing System, Binding Material Mixing Base, and Surgical Bone Cement Mixing System", naming Ronnie Burchett as inventor, and filed concurrently herewith. Such U.S. patent application Ser. No. 09/503,946 is herein Incorporated by reference as evidencing one manner of design for base 34.

It is understood that end cap 14, nozzle 18, base 34 and funnel 31 each form a bone cement mixing and delivery system body. As such, each body comprises a bone cement system component. Furthermore, container 16 further comprises a bone cement system component.

Figure 4:
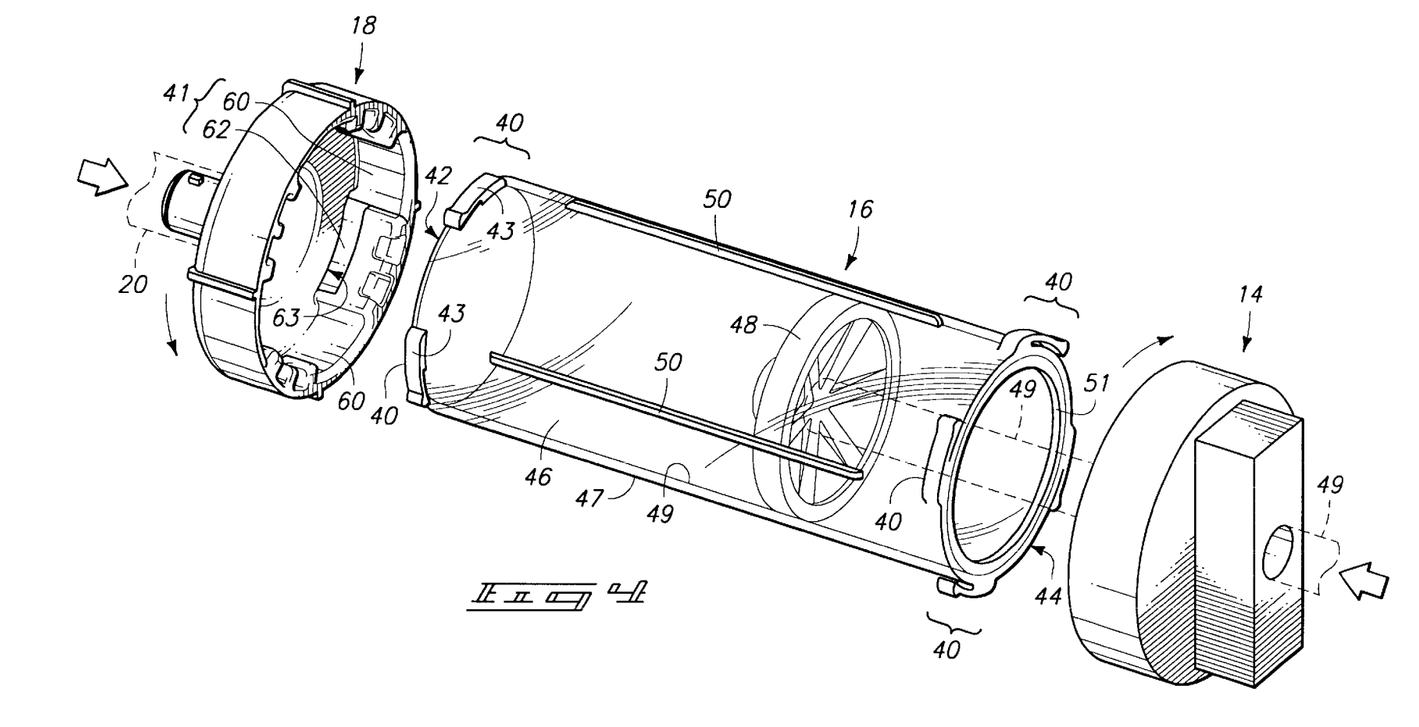
FIG. 4 is an enlarged exploded perspective view of the nozzle, the dispensing container and an end cap.

Referring to FIG. 4, a first end 42 of dispensing container 16 is positioned within nozzle 18 and a second end 44 is positioned within end cap 14. Both connector assemblies use the same connecting technique identified by male portion 40 and female portion. 41. Hence, end cap 14 includes female portion 41 even though it is not clearly shown in FIG. 4. Dispensing container 16 comprises a cylindrical tube 46 having an outer surface 47 and an inner surface 52. Inner surface 52 supports piston head 48 for sliding and sealing cooperation within dispensing container 16. A peripheral lip 51 extends inwardly from inner surface 52 at second end 44, establishing a smaller radius than inner surface 52, and thereby retaining piston 48 within dispensing container 16. A plurality of gripping ribs 50 are radially spaced from each other on outer surface 47 and extend longitudinally thereon. The outer surface 47 further comprises male portions 40 integrally formed adjacent first and second ends 42, 44. A piston rod 49 (shown in phantom) from the extrusion gun 12 (FIG. 1) engages the piston head 48 through end cap 14 to move piston 48 within container 16 in order to delivery cement through nozzle 18.

With reference to FIGS. 5–10, the connector assembly comprising male and female portions 40, 41, and the cooperation between the two, are described in detail. For exemplary purposes only, male portions 40 will be shown and discussed in reference to the first body comprising dispensing container 16 and female portions 41 will be shown and discussed in reference to the second body comprising the nozzle 18. However, it will be understood that male portion 40 and female portion 41 can be formed on other interchangeable components of a bone cement mixing and delivery system.

Figure 5:
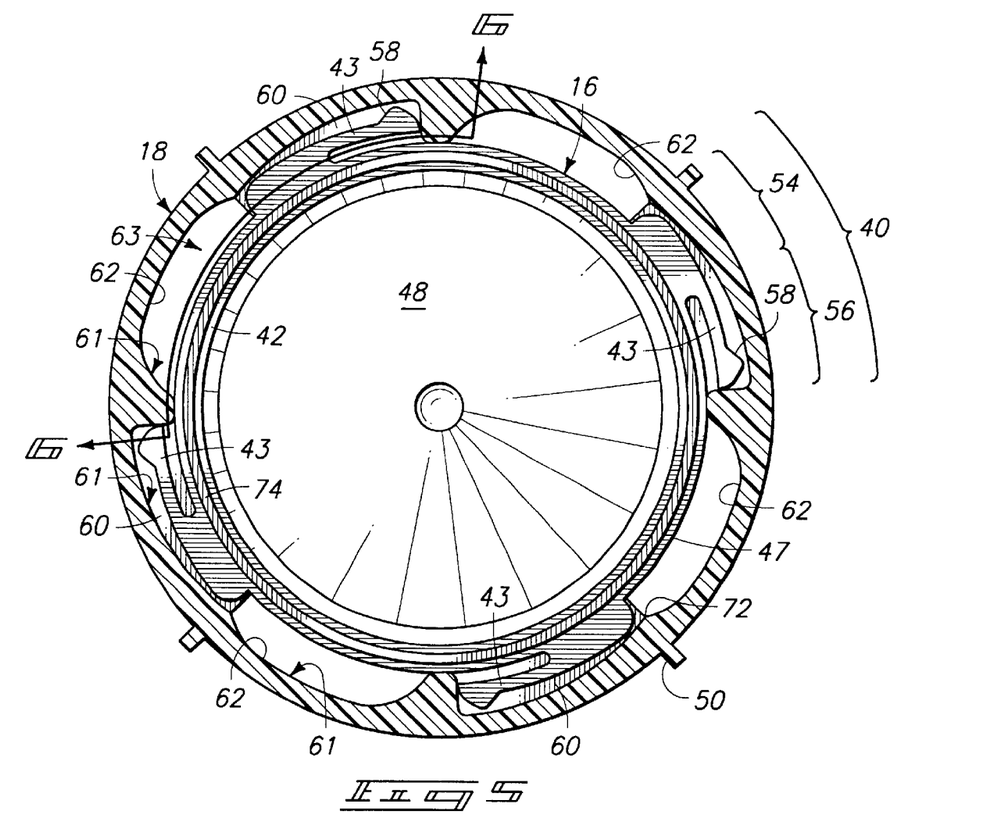
FIG. 5 is a cross-sectional view of the bone cement dispensing container and nozzle illustrating a first stage cooperation of positioning the components together according to one aspect of the invention.

Referring to FIG. 5, a first stage cooperation is illustrated. FIG. 5 is taken along line 9—9 of FIG. 1, but showing male portion 40 and female portion 41 axially received together in assembly, but prior to rotating such into interlocking engagement therebetween. The male portion 40 comprises a proximal end 54 that anchors each male portion 40 to outer surface 47 and a distal end 56 extending outwardly and arcuately along outer surface 47. The distal end 56 comprises a generally rectangular finger arcuately formed and spaced a distance from the outer surface 47 and directed in one of a clockwise or a counterclockwise direction. The distal end 56 is oriented perpendicular to a longitudinal axis of dispensing container 16 and terminates to form a knob 58 extending away from outer surface 47 of dispensing container 16. Distal end 56 is capable of being elastically urged in an inward direction toward the outer surface 47 and relaxed back to an original position. The male portion 40 includes an upper surface wall 66 and an engaging surface wall 64 forming opposite sides of the rectangular design. The female portion 41 comprises a receiving recess, or receiving slot 60, laterally adjacent a locking recess, or locking slot 62, formed from an inner wall 61 of nozzle 18. A ridge 72 separates recesses 60, 62 and is formed having a smaller radius in the inner wall 61 than recesses 60, 62.

As shown in FIGS. 2 and 4–11, a plurality of mold apertures 63 are formed in nozzle 18 by male fingers (not shown) extending from a mold surface that is used to mold nozzle 18. More particularly, a mold aperture 63 is formed through nozzle 18 so as to coincide with the location of each locking recess 62. Mold apertures 63 enable mold fingers to extend through nozzle 18 so as to form locking recesses 62. In this manner, the mold fingers can be retracted through nozzle 18 after molding nozzle 18, thereby reducing the complexity of the mold required to form nozzle 18.

In this first stage cooperation, dispensing container 16 and nozzle 18 are aligned for longitudinal cooperation. Nozzle 18 is received over the dispensing container 16 and male portions 40 such that each of male portions 40 slide longitudinally into an associated receiving recess 60. Male portions 40 are positioned in receiving recesses 60 with proximal ends 54 nearest locking recesses 62.

Figure 6:
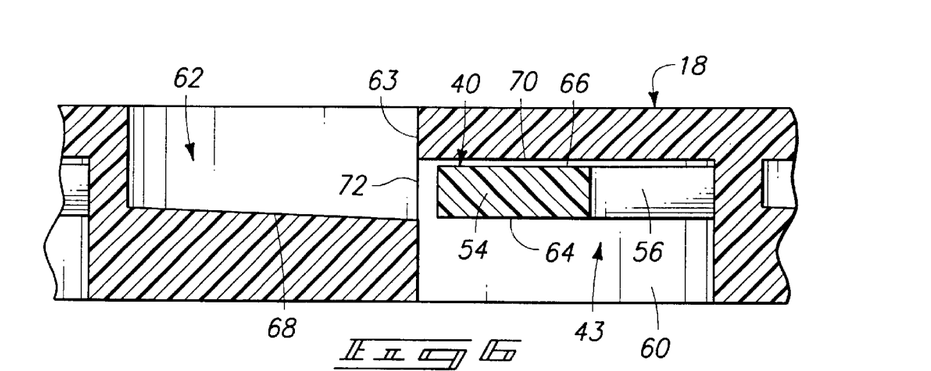
FIG. 6 is a sectional side view taken along sectional line 6—6 of the FIG. 5 container and nozzle further illustrating the first stage cooperation.

Referring to FIG. 6, receiving recess 60 and locking recess 62 share a stopping surface 70. The locking recess 62 includes a biasing surface 68 angled relative stopping surface 70. During longitudinal motion of positioning nozzle 18 over dispensing container 16, male portion 40 slides longitudinally into receiving recess 60 until upper surface wall 66 of male portion 40 abuts stopping surface 70 to impede the longitudinal motion of dispensing container 16 relative nozzle 18. At this juncture of cooperation, male portion 40 is laterally adjacent locking recess 62.

Figure 7:
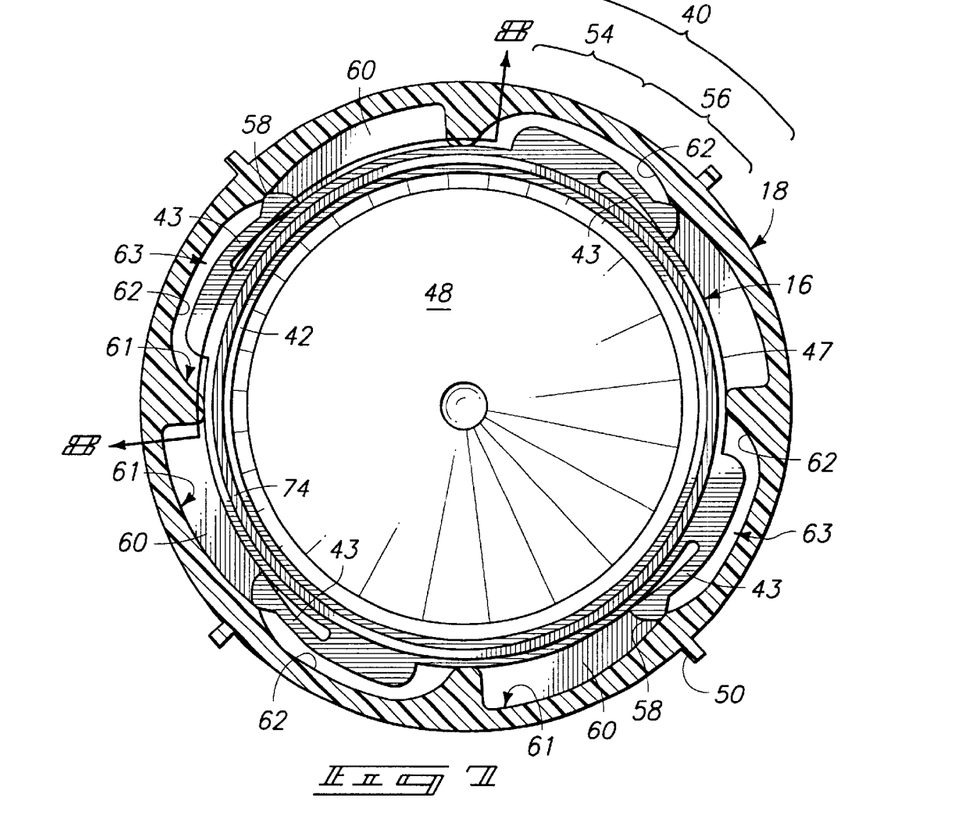
FIG. 7 is a cross-sectional view of the bone cement dispensing container and nozzle illustrating a second stage cooperation of positioning and locking the components together according to one aspect of the invention.

Referring to FIG. 7, a second stage of the cooperation between dispensing container 16 and nozzle 18 is illustrated. FIG. 7 is taken along line 9—9 of FIG. 1, but showing nozzle 18 partially rotated in interlocking engagement relative to container 16, and following axial positioning depicted in FIG. 5. At this stage of cooperation, the two components have come to rest longitudinally and now a twisting force is applied to either component to begin moving the male portion 40 into locking recess 62. As the male portion 40 begins to move into locking recess 62, the proximal end 54 moves past ridge 72 and into locking recess 62 before distal end 56. Distal end 56 engages ridge 72 with knob 58 riding along the surface of ridge 72 to act like a resistance boundary and camming the distal end 56 toward outer surface 47 of dispensing container 16. Such camming action allows distal end 56 and knob 58 to pass along and over ridge 72.

Figure 8:
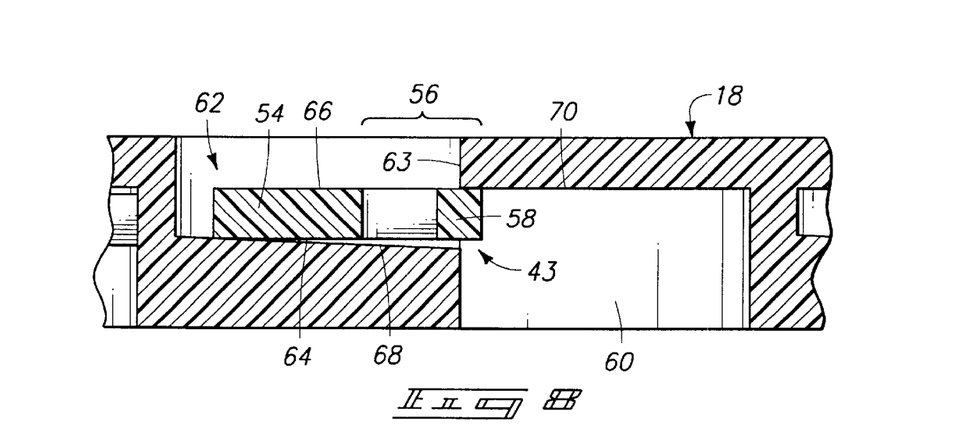
FIG. 8 is a sectional side view taken along sectional line 8—8 of the FIG. 7 container and nozzle further illustrating the second stage cooperation.

Referring to FIG. 8, in this second stage of cooperation, engaging surface wall 64 of male portion 40 contacts biasing surface 68 of locking recess 62 to apply biasing pressure on male portion 40 thereby forcing dispensing container 16 into and together with nozzle 18.

Figure 9:
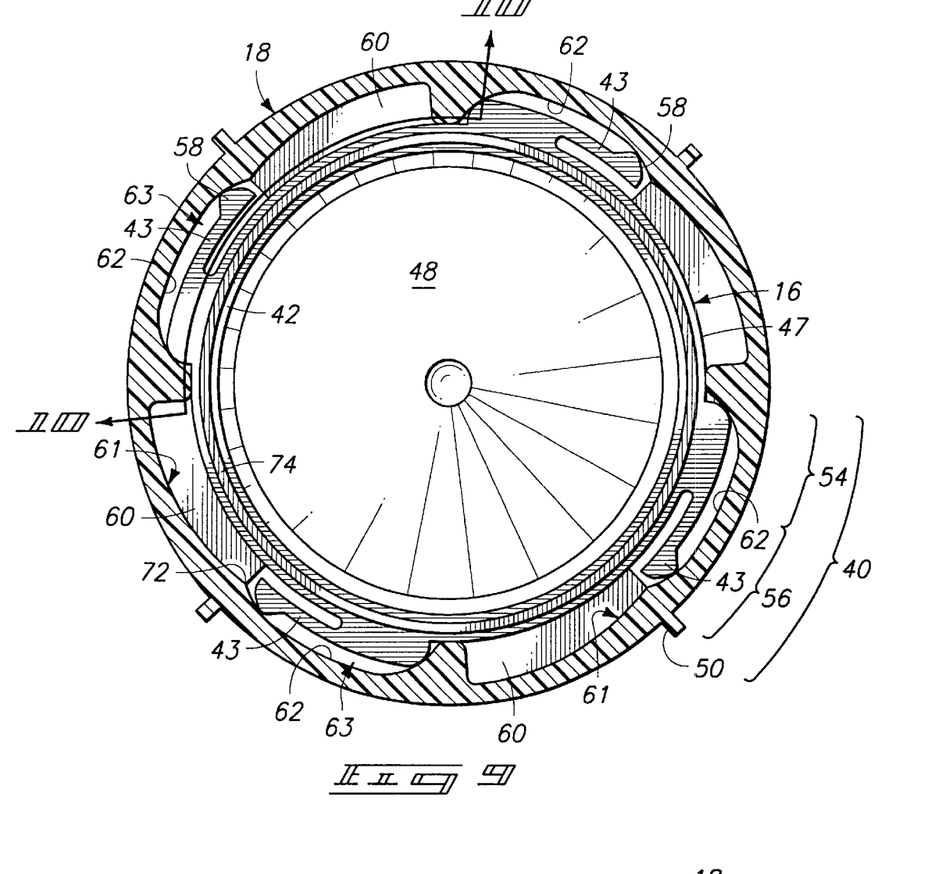
FIG. 9 is a cross-sectional view of the bone cement dispensing container and nozzle illustrating a third stage cooperation of positioning and locking the components together according to one aspect of the invention.
Figure 10:
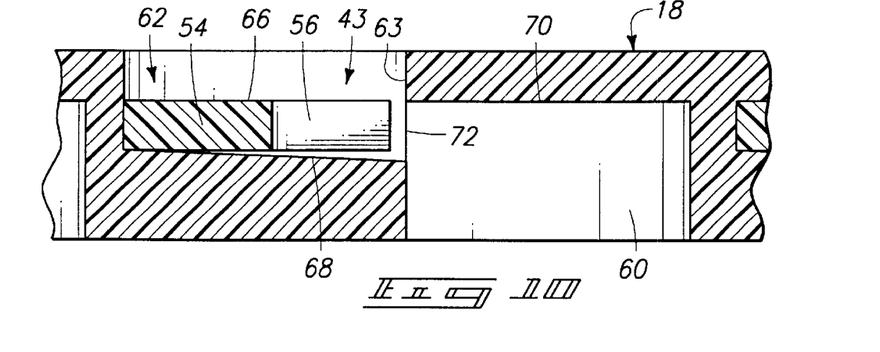
FIG. 10 is a sectional side view taken along sectional line 10—10 of the FIG. 9 container and nozzle further illustrating the third stage cooperation.

Referring to FIGS. 9 and 10, a third stage of cooperation is illustrated. FIG. 9 is taken along line 9—9 of FIG. 1 showing nozzle 18 axially loaded and rotated in interlocking engagement with container 16. Male portion 40 is shown completely resting in locking recess 62 with resilient distal end 56 having rebounded from outer surface 47 and knob 58 resting against inner wall 61 of locking recess 62. In this position, ridge 72 acts as a locking boundary preventing male portion 40 from, reentering receiving recess 60. Accordingly, dispensing container 16 is locked into place with nozzle 18.

Figure 11:
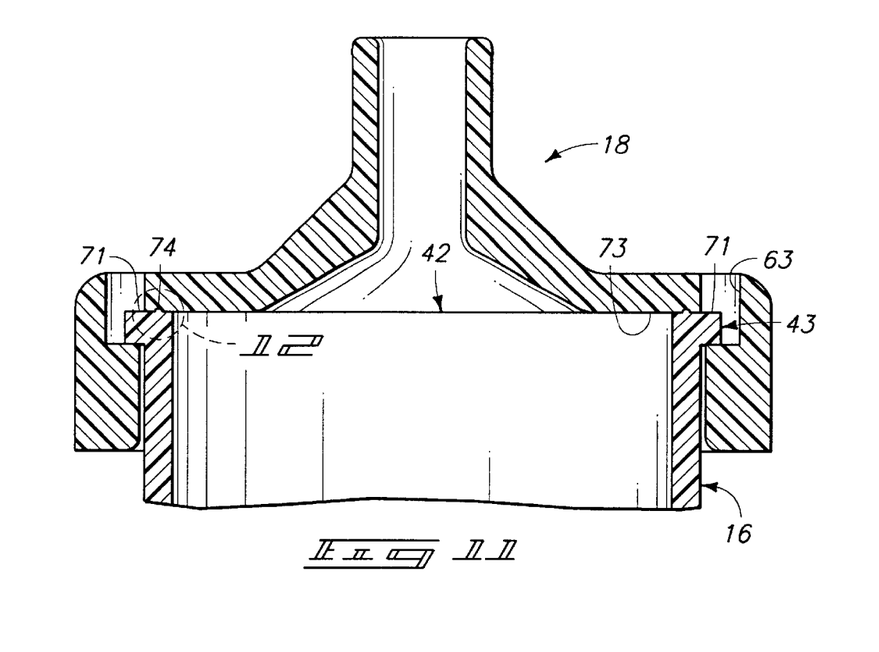
FIG. 11 is a longitudinal centerline sectional view of the nozzle positioned over a partial centerline sectional view of the container according to one aspect of the invention.

Referring to FIG. 11, first end 42 of dispensing container 16 includes an upper surface 71 which comprises a circumferential ridge 74 extending upwardly from upper surface 71 and contacts a nozzle surface 73 of nozzle 18 during cooperation.

Figure 12:
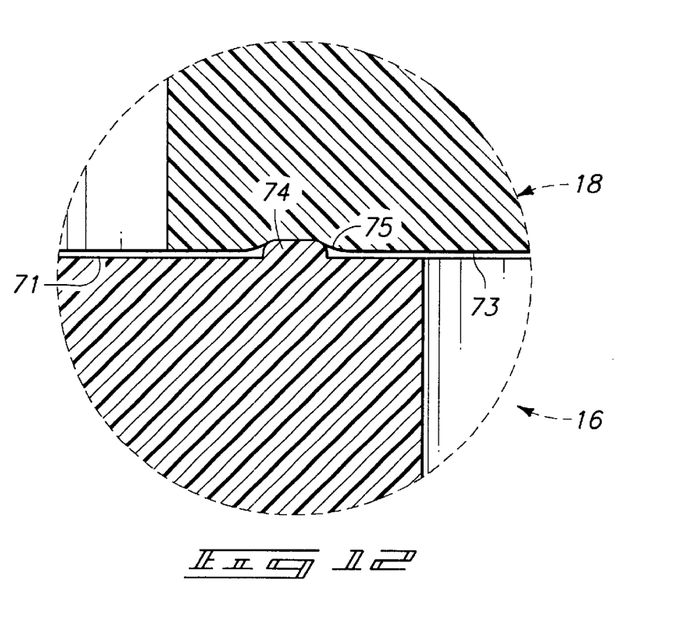
FIG. 12 is a partially enlarged view of the FIG. 11 nozzle and container illustrating an interface between the components according to one aspect of the invention.

Referring to FIG. 12, as dispensing container 16 is biased into nozzle 18, circumferential ridge 74 is driven into nozzle surface 73 to form a deformation portion 75 therein of nozzle 18 thereby forming a fluid containment system. Exemplary dimensions for the peripheral seal 74 include a height of $10/1000$ inch (extending above upper surface 71) and a width of $20/1000$ inch. The deformation portion 75 is achieved by using a softer material to form the nozzle 18 than the polycarbonate material used to form the dispensing container 16. An exemplary material for the nozzle 18 comprises a nylon-based material.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A connector assembly for a fluid containment system, comprising:
   a first body including a male portion having a plurality of fingers extending outwardly and arcuately along the body, a terminating portion of each finger elastically urgable in an inward direction; and
   a second body including a female portion having a plurality of longitudinally extending receiving slots along an inner surface of the female portion, each longitudinal slot positioned to axially receive in assembly a respective one of the fingers, and at least one recess formed in the female portion inner surface adjacent and arcuately offset from each longitudinal slot;
   wherein the first body is axially loaded into the second body by inserting the fingers into the slots, and the loaded first body is rotated relative to the second body, inwardly urging the fingers, and thereafter receiving at least one of the fingers within a respective recess.

2. The connector assembly of claim 1 wherein the first body comprises a bone cement mixing and delivery cartridge.

3. The connector assembly of claim 2 wherein the second body comprises a dispensing nozzle.

4. The connector assembly of claim 2 wherein the second body comprises a delivery funnel.

5. The connector assembly of claim 2 wherein the second body comprises a support base for a bone cement mixing system.

6. The connector assembly of claim 2 wherein the second body comprises an end cap of a bone cement dispensing gun.

7. The connector assembly of claim 1 wherein the first body comprises a container configured to carry surgical bone cement.

8. The connector assembly of claim 1 wherein all of the fingers extend arcuately in one of a clockwise or a counterclockwise direction.

9. A connector assembly for a fluid containment system, comprising:
   a first body including a male portion having a plurality of fingers extending outwardly and arcuately along the body, a terminating portion of each finger elastically urgable in an inward direction; and
   a second body including a female portion having a plurality of longitudinally extending receiving slots along an inner surface of the female portion, each longitudinal slot positioned to axially receive in assembly a respective one of the fingers, and at least one recess formed in the female portion inner surface adjacent and arcuately offset from each longitudinal slot; one or more of the at least one recess including a biasing surface tapered in a direction transverse to an axis of rotational engagement between the first body and the second body;
   wherein the first body is axially loaded into the second body by inserting the fingers into the slots, and the loaded first body is rotated relative to the second body, inwardly urging the fingers, and thereafter receiving the fingers within a respective recess.

10. The connector assembly of claim 9 wherein one tapered recess of the at least one recess is configured to urge the first body and the second body together into sealing engagement therebetween.

11. A connector assembly for a fluid containment system, comprising:
   a first body including a male portion having a plurality of fingers extending outwardly and arcuately along the body, a terminating portion of each finger elastically urgable in an inward direction;
   a second body including a female portion having a plurality of longitudinally extending receiving slots along an inner surface of the female portion, each longitudinal slot positioned to axially receive in assembly a respective one of the fingers, and at least one recess formed in the female portion inner surface adjacent and arcuately offset from each longitudinal slot; and
   a ridge including a biasing surface extending inwardly and arcuately of the female portion of the second body and provided between each slot and adjacent recess, the biasing surface configured to urge the finger inwardly during rotation of the first body and the second body;
   wherein the finger relaxes outwardly upon being received over the biasing surface and into the recess.

12. A connector assembly for a fluid containment system, comprising:
   a first body comprising a container configured to carry surgical bone cement including a male portion having a plurality of fingers extending outwardly and arcuately along the body, a terminating portion of each finger elastically urgable in an inward direction; and
   a second body including a female portion having a plurality of longitudinally extending receiving slots along an inner surface of the female portion, each longitudinal slot positioned to axially receive in assembly a respective one of the fingers, and at least one recess formed in the female portion inner surface adjacent and arcuately offset from each longitudinal slot;
   wherein the first body is axially loaded into the second body by inserting the fingers into the slots, and the loaded first body is rotated relative to the second body, inwardly urging the fingers, and thereafter receiving at least one of the fingers within a respective recess; and
   wherein a leading edge of the container comprises a circumferential ridge formed from a substantially hard material, wherein the second body is formed from a relatively compliant material, and wherein the circumferential ridge is urged into biased and sealing engagement with the second body upon rotatable engagement of the second body with the container.

13. The connector assembly of claim 12 wherein each recess comprises a biasing surface tapered In a direction transverse to an axis of rotational engagement between the first body and the second body and configured to urge the container and the second body together into sealing engagement therebetween.

14. A bone cement mixing and delivery system, comprising:
   a bone cement container including a male portion having a plurality of fingers extending radially outwardly and arcuately along the container, a terminating end portion of each finger elastically urgable in an inward direction; and a bone cement mixing and delivery system body including a female portion having a plurality of longitudinally extending receiving slots along an inner surface of the female portion, each longitudinal slot positioned to axially receive in assembly a respective one of the fingers, and at least one recess formed in the female portion inner surface adjacent and arcuately offset from each longitudinal slot;

wherein the container is axially loaded into the body by inserting the fingers into the slots, and the loaded container is rotated relative to the body, inwardly urging at least one of the fingers, and receiving the within at least one finger respective recess.

15. The system of claim 14 wherein the bone cement container comprises a cartridge.

16. The system of claim 15 wherein the body comprises a dispensing nozzle.

17. The system of claim 15 wherein the body comprises a delivery funnel.

18. The system of claim 15 wherein the body comprises a support base for a bone cement mixing system.

19. The system of claim 15 wherein the body comprises an end cap of a bone cement dispensing gun.

20. The system of claim 15 wherein each recess includes a biasing surface tapered in a direction extending transverse to an axis of rotational engagement between the body and the bone cement container.

21. The system of claim 20 further comprising a ridge including a biasing surface extending inwardly and arcuately of the female portion of the body and provided between each slot and adjacent recess, the biasing surface configured to urge the finger inwardly during rotation of the bone cement container and the body, wherein the finger relaxes outwardly upon being received over the biasing surface and into the recess.

22. The system of claim 20 wherein a leading edge of the container comprises a circumferential ridge formed from a substantially hard material, wherein the body is formed from a relatively compliant material, wherein the circumferential ridge is urged into biased and sealing. engagement with the body upon rotatable engagement of the body with the container.

23. The system of claim 22 wherein each recess comprises a tapered surface configured to urge the container and the body together into sealing engagement therebetween.

24. A bone cement mixing and delivery system, comprising:

a bone cement container comprising a cartridge including a male portion having a plurality of fingers extending radially outwardly and arcuately along the container, a terminating end portion of each finger elastically urgable in an inward direction; and a bone cement mixing and delivery system body including a female portion having a plurality of longitudinally extending receiving slots along an inner surface of the female portion, each longitudinal slot positioned to axially receive in assembly a respective one of the fingers, and at least one recess formed in the female portion inner surface adjacent and arcuately offset from a respective longitudinal slot and including a biasing surface tapered in a direction extending transverse to an axis of rotational engagement between the body and the bone cement container;

wherein the container is axially loaded into the body by inserting the fingers into the slots, and the loaded container is rotated relative to the body, inwardly urging at least one of the fingers, and receiving the within at least one finger respective recess; and wherein the tapered recess is configured to urge the bone cement container and the body together into sealing engagement therebetween.

25. A bone cement containment system, comprising;

a bone cement container including an end portion having a plurality of fingers extending outwardly and arcuately along an outer surface of the container, a distal portion of each finger elastically urgable in an inward direction; and a bone cement containment system component having an end portion including a plurality of longitudinal extending receiving slots along an inner surface, each longitudinal slot positioned to axially receive one of the fingers, and at least one recess formed in an inner surface adjacent and arcuately offset from a respective longitudinal slot.

26. The containment system of claim 25 wherein the container is axially loaded into the component by inserting the fingers into the slots, and the loaded container is rotated relative to the component, inwardly urging at least one of the fingers, and receiving the at least one finger within the respective recess.

27. A bone cement containment system, comprising;

a bone cement container including an end portion having a plurality of fingers extending outwardly and arcuately along an outer surface of the container, a distal portion of each finger elastically urgable in an inward direction; and a bone cement containment system component having an end portion including a plurality of longitudinal extending receiving slots along an inner surface, each longitudinal slot positioned to axially receive one of the fingers, and at least one recess formed in an inner surface adjacent and arcuately offset from a respective longitudinal slot;

wherein one of the least one recess includes a tapered engagement surface configured to urge the container and the component together into sealing engagement therebetween.

28. The containment system of claim 27 further comprising a ridge formed along a leading edge of the end portion on the container, wherein the container is formed from a relatively ridged material and the component is formed from a relatively compliant material, and wherein the ridge is urged into biased and sealing engagement with the component upon rotatable engagement of the container with the component.

* * * * *